(12) United States Patent
Arenson et al.

(10) Patent No.: US 7,424,090 B2
(45) Date of Patent: *Sep. 9, 2008

(54) APPARATUS FOR ACQUISITION OF CT DATA WITH PENUMBRA ATTENUATION CALIBRATION

(75) Inventors: Jerome Stephen Arenson, Haifa (IL); David Ruimi, Netanya (IL); Oded Meirav, Haifa (IL); Robert Harry Armstrong, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/745,765

(22) Filed: May 8, 2007

(65) Prior Publication Data

US 2007/0206720 A1 Sep. 6, 2007

Related U.S. Application Data

(63) Continuation of application No. 10/904,116, filed on Oct. 25, 2004, now Pat. No. 7,260,171.

(51) Int. Cl.
*A61B 6/03* (2006.01)
(52) U.S. Cl. .......................................... 378/19; 378/16
(58) Field of Classification Search ................ 378/16, 378/19
See application file for complete search history.

(56) References Cited

U.S. PATENT DOCUMENTS

| 5,165,100 | A | 11/1992 | Hsieh et al. |
| 5,400,378 | A | 3/1995 | Toth |
| 5,608,776 | A | 3/1997 | Hsieh |
| 5,684,855 | A | 11/1997 | Aradate et al. |
| 6,173,039 | B1 | 1/2001 | Hampel et al. |
| 6,185,274 | B1 * | 2/2001 | Kinno et al. ............... 378/98.8 |
| 6,917,665 | B2 | 7/2005 | Nakanishi et al. |
| 7,260,171 | B1 * | 8/2007 | Arenson et al. ............... 378/16 |
| 2002/0071517 | A1 | 6/2002 | Hoffman |
| 2003/0063266 | A1 | 4/2003 | Leenders et al. |
| 2003/0195416 | A1 | 10/2003 | Toth |
| 2004/0264627 | A1 | 12/2004 | Besson |
| 2006/0056581 | A1 | 3/2006 | Hoffman et al. |

* cited by examiner

*Primary Examiner*—Chih-Cheng G Kao
(74) *Attorney, Agent, or Firm*—Ziolkowski Patent Soultions Group, SC (57) ABSTRACT

The present invention is a directed method and apparatus for collimating a radiation beam such that the full intensity of the radiation beam does not impinge detectors of a radiation detector assembly that are particularly susceptible to saturation or over-ranging. This collimation can be dynamically adjusted on a per view basis using empirical or scout scan data.

20 Claims, 4 Drawing Sheets

APPARATUS FOR ACQUISITION OF CT DATA WITH PENUMBRA ATTENUATION CALIBRATION

CROSS REFERENCE TO RELATED APPLICATIONS

The present application is a continuation of and claims priority of U.S. Ser. No. 10/904,116 filed Oct. 25, 2004, the disclosure of which is incorporated herein by reference.

BACKGROUND OF THE INVENTION

The present invention relates generally to radiographic imaging and, more particularly, to a method and system of dynamically controlling collimation of a radiation fan beam to limit x-ray flux to detectors of a x-ray detector assembly susceptible to saturation or over-ranging. The present invention further relates to correcting data from saturated detectors using data from intensity calibration detectors.

Typically, in radiographic systems, an x-ray source emits x-rays toward a subject or object, such as a patient or a piece of luggage. Hereinafter, the terms "subject" and "object" may be interchangeably used to describe anything capable of being imaged. The x-ray beam, after being attenuated by the subject, impinges upon an array of radiation detectors. The intensity of the radiation beam received at the detector array is typically dependent upon the attenuation of the x-rays through the scanned object. Each detector of the detector array produces a separate signal indicative of the attenuated beam received by each detector. The signals are transmitted to a data processing system for analysis and further processing which ultimately produces an image.

In a similar fashion, radiation detectors are employed in emission imaging systems such as used in nuclear medicine (NM) gamma cameras and Positron Emission Tomography (PET) systems. In these systems, the source of radiation is no longer an x-ray source, rather it is a radiopharmaceutical introduced into the body being examined. In these systems each detector of the array produces a signal in relation to the localized intensity of the radiopharmaceutical concentration in the object. Similar to conventional x-ray imaging, the strength of the emission signal is also attenuated by the interlying body parts. Each detector element of the detector array produces a separate signal indicative of the emitted beam received by each detector element. The signals are transmitted to a data processing system for analysis and further processing which ultimately produces an image.

In most computed tomography (CT) imaging systems, the x-ray source and the detector array are rotated about a gantry encompassing an imaging volume around the subject. X-ray sources typically include x-ray tubes, which emit the x-rays as a fan or cone beam from the anode focal point. X-ray detector assemblies typically include a collimator for reducing scattered x-ray photons from reaching the detector, a scintillator adjacent to the collimator for converting x-rays to light energy, and a photodiode adjacent to the scintillator for receiving the light energy and producing electrical signals therefrom. Typically, each scintillator of a scintillator array converts x-rays to light energy. Each photodiode detects the light energy and generates a corresponding electrical signal. The outputs of the photodiodes are then transmitted to the data acquisition system and then to the processing system for image reconstruction.

Conventional CT imaging systems utilize detectors that convert x-ray photon energy into current signals that are integrated over a time period, then measured and ultimately digitized. A drawback of such detectors is their inability to provide independent data or feedback as to the energy and incident flux rate of photons detected. That is, conventional CT detectors have a scintillator component and photodiode component wherein the scintillator component illuminates upon reception of x-ray photons and the photodiode detects illumination of the scintillator component and provides an integrated electrical current signal as a function of the intensity and energy of incident x-ray photons. While it is generally recognized that CT imaging would not be a viable diagnostic imaging tool without the advancements achieved with conventional CT detector design, a drawback of these integrating detectors is their inability to provide energy discriminatory data or otherwise count the number and/or measure the energy of photons actually received by a given detector element or pixel. Accordingly, recent detector developments have included the design of an energy discriminating detector that can provide photon counting and/or energy discriminating feedback. In this regard, the detector can be caused to operate in an x-ray counting mode, an energy measurement mode of each x-ray event, or both.

These energy discriminating detectors are capable of not only x-ray counting, but also providing a measurement of the energy level of each x-ray detected. While a number of materials may be used in the construction of an energy discriminating detector, including scintillators and photodiodes, direct conversion detectors having an x-ray photoconductor, such as amorphous selenium or cadmium zinc telluride, that directly convert x-ray photons into an electric charge have been shown to be among the preferred materials. A drawback of photon counting detectors, however, is that these types of detectors have limited count rates and have difficulty covering the broad dynamic ranges encompassing very high x-ray photon flux rates typically encountered with conventional CT systems. Generally, a CT detector dynamic range of 1,000,000 to one is required to adequately handle the possible variations in photon flux rates. In the very fast scanners now available, it is not uncommon to encounter x-ray flux rates of over $10^8$ photons/mm$^2$/sec when no object is in the scan field, with the same detection system needing to count only tens of photons that manage to traverse the center of large objects.

The very high x-ray photon flux rates ultimately lead to detector saturation. That is, these detectors typically saturate at relatively low x-ray flux levels. This saturation can occur at detector locations wherein small subject thickness is interposed between the detector and the radiographic energy source or x-ray tube. It has been shown that these saturated regions correspond to paths of low subject thickness near or outside the width of the subject projected onto the detector array. In many instances, the subject is more or less cylindrical in the effect on attenuation of the x-ray flux and subsequent incident intensity to the detector array. In this case, the saturated regions represent two disjointed regions at extremes of the detector array. In other less typical, but not rare instances, saturation occurs at other locations and in more than two disjointed regions of the detector. In the case of a cylindrical subject, the saturation at the edges of the array can be reduced by the imposition of a bowtie filter between the subject and the x-ray source. Typically, the filter is constructed to match the shape of the subject in such a way as to equalize total attenuation, filter and subject, across the detector array. The flux incident to the detector is then relatively uniform across the array and does not result in saturation. What can be problematic, however, is that the bowtie filter may not be optimum given that a subject population is significantly less than uniform and not exactly cylindrical in shape nor centrally located in the x-ray beam. In such cases, it is possible for one or more disjointed regions of saturation to occur or conversely to over-filter the x-ray flux and unnecessarily create regions of very low flux. Low x-ray flux in the projection results in a reduction in information content which will ultimately contribute to unwanted noise in the reconstructed image of the subject.

Moreover, a system calibration method common to most CT systems involves measuring detector response with no subject whatsoever in the beam. This "air cal" reading from each detector element is used to normalize and correct the preprocessed data that is then used for CT image reconstruction. Even with ideal bowtie filters, high x-ray flux now in the central region of the detector array could lead to detector saturation during the system calibration phase.

A number of imaging techniques have been proposed to address saturation of any part of the detector. These techniques include maintenance of low x-ray flux across the width of a detector array, for example, by modulating tube current or x-ray voltage during scanning. However, this solution leads to increased scanned time. That is, there is a penalty that the acquisition time for the image is increased in proportion to the nominal flux needed to acquire a certain number of x-rays that meet image quality requirements. Other solutions include the implementation of over-range algorithms that may be used to generate replacement data for the saturated data. However, these algorithms may imperfectly replace the saturated data as well as contribute to the complexity of the CT system.

It would therefore be desirable to design a method and system to collimate a radiation fan beam to limit x-ray flux to detectors of an x-ray detector assembly susceptible to saturation or over-ranging.

BRIEF DESCRIPTION OF THE INVENTION

The present invention is a directed method and apparatus for collimating a radiation beam such that the full intensity of the radiation beam does not impinge upon detectors of a radiation detector assembly that are particularly susceptible to saturation or over-ranging that overcomes the aforementioned drawbacks. This collimation can be dynamically adjusted on a per view basis using empirical or scout scan data.

The present invention is particularly applicable to detectors that count and tag radiating energy attenuated by a subject. The method and system are designed to dynamically control collimation of the radiation beam to limit exposure to a full intensity radiation beam so as to prevent saturation of portions of a radiation detector assembly during high flux conditions. Moreover, the present invention is designed to control collimation so as to accommodate low flux rate conditions such that detection efficiency and image quality is not sacrificed when lower flux is experienced by the detector.

Therefore, in accordance with one aspect of the present invention, a CT system includes a radiation source configured to project a radiation beam toward a subject to be scanned and a collimator configured to collimate the radiation beam. The CT system further includes a multi-row detector configured to detect radiation emitted by the radiation source and attenuated by the subject and a controller operationally connected to the collimator and configured to control the collimator so as to limit exposure of a full intensity of the radiation beam to less than all detector rows of the multi-row CT detector.

In accordance with another aspect, the present invention includes a radiographic imaging system having a multi-slice CT detector configured to detect radiation emitted by a radiation source and attenuated by a subject to be imaged. The imaging system further has a slice-width collimator disposed between the radiation source and the multi-slice CT detector. The slice-width collimator is configured to collimate a radiation beam in a direction parallel to a long axis of the subject such that full intensity of the radiation beam is prevented from impinging upon at least one intensity calibration detector row of the multi-slice CT detector.

According to another aspect of the present invention, a CT detector assembly is disclosed and has a plurality of imaging CT detectors arranged into multiple CT detector rows. Data collected by the plurality of imaging CT detectors is used for image reconstruction. The CT detector assembly further has a plurality of saturation correction CT detectors arranged into one or more saturation correction detector rows. Each saturation correction CT detector is constructed to over-range at an x-ray flux rate greater than that at which an imaging CT detector saturates.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other radiation energy sources.

Figure 1:
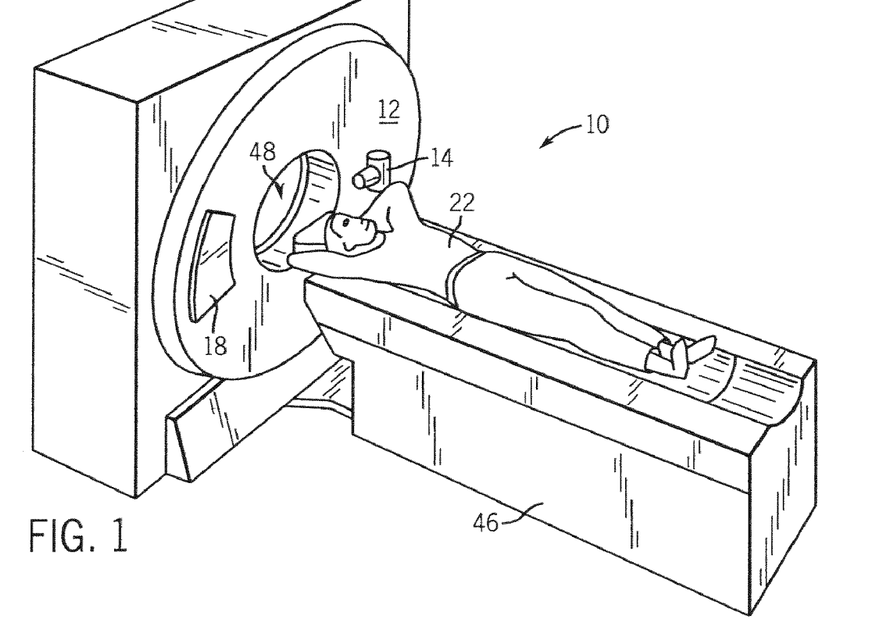
FIG. 1 is a pictorial view of a CT imaging system.
Figure 2:
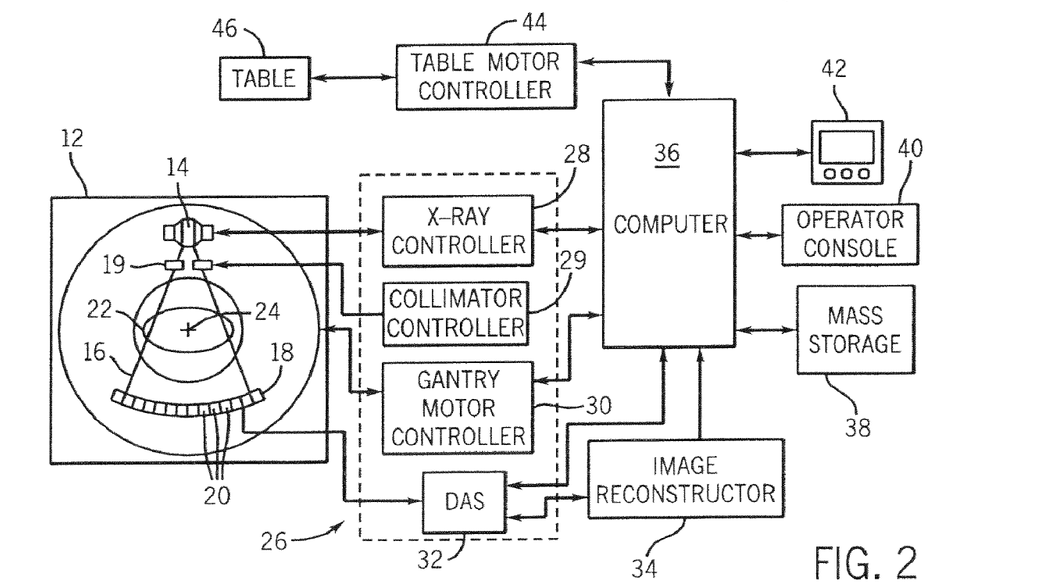
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly 18 on the opposite side of the gantry 12. The beam of x-rays is collimated by a collimator 19. Detector assembly 18 is formed by a plurality of detectors 20 which together sense the projected x-rays that pass through a medical patient 22. Each detector 20 produces an electrical signal that represents the intensity of an impinging x-ray beam and may also be capable of providing photon or x-ray count data and energy level, and hence the attenuated beam as it passes through the patient 22. During a scan to acquire x-ray projection data, gantry 12 and the components mounted thereon rotate about a center of rotation 24.

Figure 3:
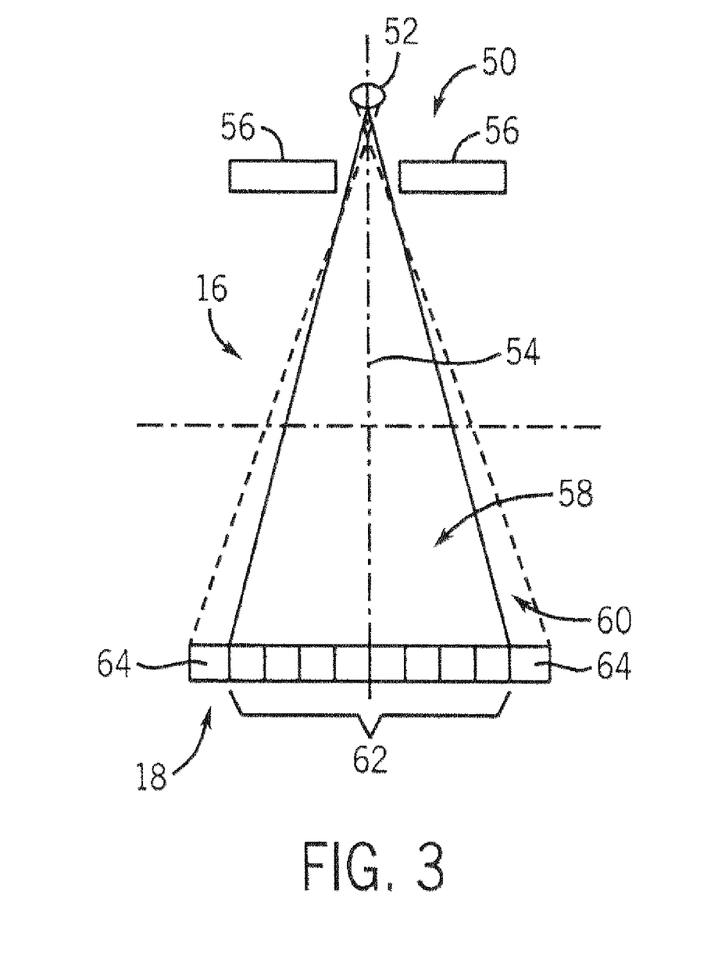
FIG. 3 is a schematic diagram of a CT imaging system incorporating a slice-width collimator in accordance with the present invention.

Rotation of gantry 12 and the operation of x-ray source 14 are governed by a control mechanism 26 of CT system 10. Control mechanism 26 includes an x-ray controller 28 that provides power and timing signals to an x-ray source 14, a gantry motor controller 30 that controls the rotational speed and position of gantry 12, and a collimator controller 29 that controls collimator 19 to collimate the x-ray beam in the x (as shown in FIG. 2) and z directions (as shown in FIG. 3). A data acquisition system (DAS) 32 in control mechanism 26 reviews data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated display screen 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

The present invention is directed to a collimator assembly and corresponding control to limit radiation exposure to a radiation detector that may be incorporated with the CT system described above or other radiographic systems, such as x-ray systems or general purpose radiation detectors.

Generally, high-sensitivity photon counting radiation detectors are constructed to have a relatively low dynamic range. This is generally considered acceptable for conventional photon counting detector applications since high flux conditions typically do not occur. In CT detector designs, low flux detector readings through the subject are typically accompanied by areas of high irradiation in air, and/or within the contours of the scan subject requiring CT detectors to have very large dynamic range responses. Moreover, the exact measurement of photons in these high-flux regions is less critical than that for low-flux areas where each photon contributes an integral part to the total collected photon statistics. Notwithstanding that the higher flux areas may be of less clinical or diagnostic value, images reconstructed with over-ranging or saturated detector channel data can be prone to artifacts. As such, the handling of high-flux conditions is also important.

The present invention includes an x-ray flux management control designed to prevent saturation of detector channels characterized by low dynamic range such as photon counting/energy discriminating x-ray detection systems. Dynamic range of a detector channel defines the range of x-ray flux levels that the detector channel can handle to provide meaningful data at the low-flux end and not experience over-ranging or saturating at the high flux end. Notwithstanding the need to prevent over-ranging, to provide diagnostically valuable data, the handling of low-flux conditions, which commonly occur during imaging through thicker cross-sections and other areas of limited x-ray transmission, is also critical in detector design. As such, the x-ray flux management control described herein is designed to satisfy both high flux and low flux conditions.

Accordingly, the present invention includes a system and method to dynamically and automatically control collimation of a radiation beam during imaging such that low-flux as well as high-flux rate conditions are optimally addressed.

Referring now to FIG. 3, a block schematic diagram illustrates operation of a slice-width collimator according to the present invention. Specifically, collimator 50 is designed to collimate x-ray beam 16. Radiation x-ray beam 16 emanates from focal spot 52 centered about axis 54 toward a subject to be imaged and detector array 18. Detector array 18 is a multi-slice detector and, as such, includes multiple rows of detectors. The rows stack-up in the z-direction which is parallel to the long axis of the subject to be imaged. Collimator 50, as a slice-width collimating device, collimates x-ray beam 16 in the z-direction so as to limit exposure to a full intensity of the x-ray beam. In this regard, collimator 50 includes a pair of collimating elements 56. The collimating elements may be controlled independently or in tandem to collimate x-ray beam 16. Additionally, collimation of the x-ray beam may be controlled dynamically during data acquisition on a per view basis, a preferred method for employment in single-slice CT systems.

In recognition that all detectors in the detector array 18 have a limited dynamic range, the collimating elements 56 are controlled such that the collimator 50 limits the full intensity of the radiation beam to less than all the detector rows. As such, the radiation beam 16 is characterized by a full intensity region 58 and a penumbral region 60 extending therefrom. The full intensity region 58 only impinges upon the central detector rows 62 whereas the penumbral region 60 extends to the outer detector rows 64. In the illustrated example, the radiation beam is collimated such that the full intensity region 58 impinges on all but the two outermost rows 64 of detector assembly 18. As such, these two outer rows 64 are exposed to a lower radiation dose than the central detector rows 62. It is contemplated that collimating elements 56 may be controlled such that the full intensity portion 58 of the radiation beam extends to all but a single outer detector row. Additionally, the radiation beam may also be collimated such that more than a single outer row at each end of the detector array receives low level x-ray flux.

Limiting the full intensity of the radiation beam to less than all the detector rows allows the detectors impinged by only the penumbral region of the radiation beam to be used as calibration detectors. That is, when the central detector rows (full intensity rows) saturate or over-range, data from the outer detector rows (penumbral rows) is still valid as these detectors have not saturated as a result of being exposed to much lower x-ray flux. As a result, the data readings of the outer detectors rows may be used for intensity calibration of the over-ranging or saturated detector rows through data interpolation. That is, the output of a saturated detector or detector row may be determined from the output of non-saturated detectors. From the dose applied to the subject, the degree and width of collimation, and a priori knowledge of the scan subject, it is possible to interpolate useful output from saturated detectors. Additionally, this can be achieved without increasing radiation dose to the subject. It is also contemplated that a scout scan can be carried out to determine a desired radiation dose profile.

As referenced above, the collimating elements may be controlled to define an asymmetric collimation of the radiation beam. This may be achieved by independently moving the collimation elements or moving both collimation elements relative to the focal spot. This asymmetric shift to the slice-width collimator allows for dynamic control of the fan beam to define the coverage of the full intensity portion and the penumbral portion in a manner tailored to a given scan subject or view. For example, applying an asymmetric shift to the slice-width collimator so as to define the full intensity of the radiation beam to impinge on all but one outermost detector row, z-coverage loss is limited to 1/N, where N is the total number of detector rows in the z-direction. This can be advantageous for helical scans wherein intensity calibration can be carried out by interpolating between adjacent sweeps of the single calibration row in the helical scan data. That is, by reducing the number of detector rows that are used for data acquisition by using the data from outermost detector rows for intensity calibration, z-coverage of the detector array is reduced. As such, table increments must be reduced or additional detector rows added to the array. As such, if collimation is carried out to block exposure to the full intensity of the radiation beam at both longitudinal edges of the detector array, a 2/N loss in z-coverage occurs. Since adding detector rows is difficult on a per scan basis, an increase in table incrementation is more likely. As such, for helical scans, by asymmetrically shifting the radiation beam such that only one detector row is characterized as a calibration row and performing intensity calibration on a per sweep or gantry rotation basis, z-coverage loss is only 1/N and a 1/N decrease in table speed is needed. In addition to helical scanning, intensity calibration may be achieved by interpolating a single calibration row data in multi-slice axial scans.

Figure 4:
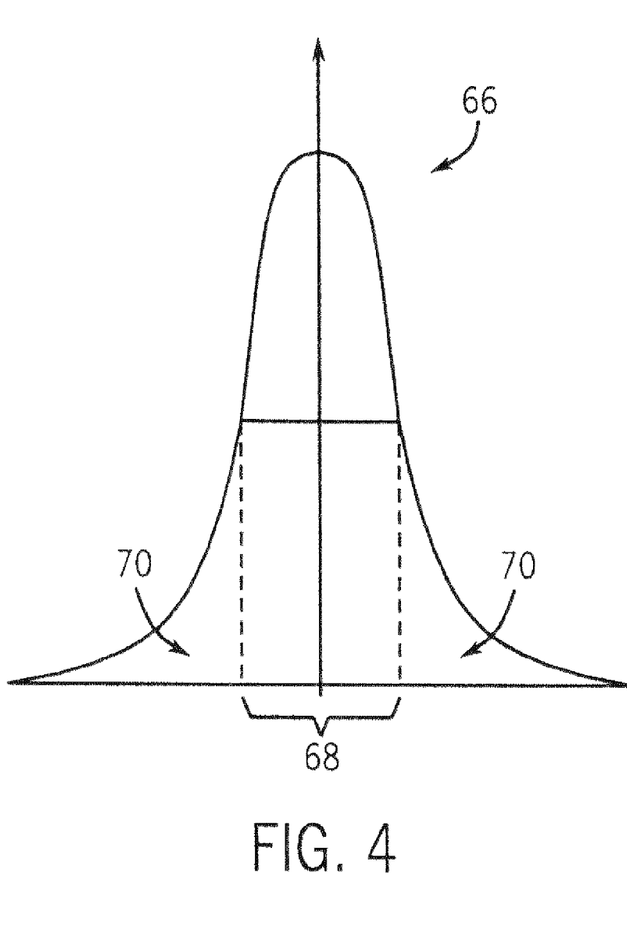
FIG. 4 is a graphical illustration of a radiation beam profile.

Referring now to FIG. 4, an exemplary radiation intensity profile 66 achievable with dynamic control of the slice-width collimator described with respect to FIG. 3 is illustrated. As shown by the height of the profile, the intensity of the radiation impinging upon the central detector rows exceeds that impinging on the outer detector rows. In this regard, the radiation profile 66 is defined by an imaging data portion 68 corresponding to the centered detector rows and a calibration data portion 70 corresponding to the outer detector rows. In the intensity profile illustrated in FIG. 4, collimation is carried out such the penumbra of the radiation beam extends to the outermost detector rows of the detector array. It is recognized that different collimation schemes will result in different radiation profiles than that illustrated in FIG. 4.

Additionally, a single calibration row may be defined along the detector array and this single calibration row is not required to be located at a z-edge of the detector array. The calibration row may be defined at any z-location along the detector array. In one embodiment, the single calibration row is selected to be in the z-center of the detector array. Collimating the radiation beam such that a center detector row is not exposed to the full intensity of the radiation beam can be difficult. As such, the present invention also contemplates the use of a pre-subject absorber at the x-ray tube or a post-subject absorber positioned after the subject and aligned with the detector row. In this regard, x-ray flux can be limited such that the center calibration row is subjected to a low level radiation flux.

It is also contemplated that unexpected shifts in calibration detector values may be addressed by reducing the impact of z-direction focal spot drift. Reducing the impact of focal spot drift can be achieved by placing attenuating material above those detectors identified as calibration detectors. To further limit the impact of focal spot drift and/or collimator positioning on data acquisition, the slice-width collimator may be controlled such that the collimating elements may be separated from one another such that the full intensity of the radiation beam impinges partly into the outermost detector rows.

Additionally, the present invention contemplates that a detector assembly can be constructed with pre-selected calibration detector rows that are thinner in the z-direction than the imaging data detector rows. For instance, the detectors of the calibration rows may be constructed to have one-fourth the z-coverage of the nominal imaging data detectors. Not only does such a construction reduce the material costs of the detector array, but the saturation characteristics of a detector is a function, in part, of its size. That is, a smaller detector will receive proportionately less x-ray flux than a nominal imaging detector which makes the smaller calibration detector less prone to saturation. Further, when coupled with the use of pre-detector attenuation material, less material is required to shadow the calibration row if constructed to be thinner in the z-direction than nominal imaging detector rows. Thinner calibration detectors also reduces the dose required to gather calibration data.

Figure 5:
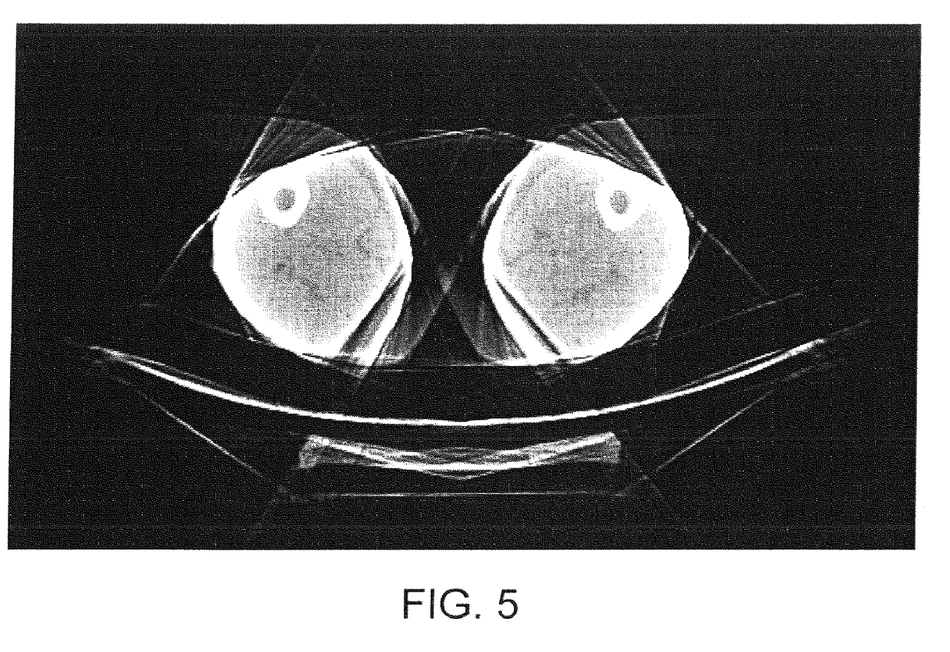
FIG. 5 is a CT image through thighs of an exemplary subject reconstructed from data acquired with saturated detectors.
Figure 6:
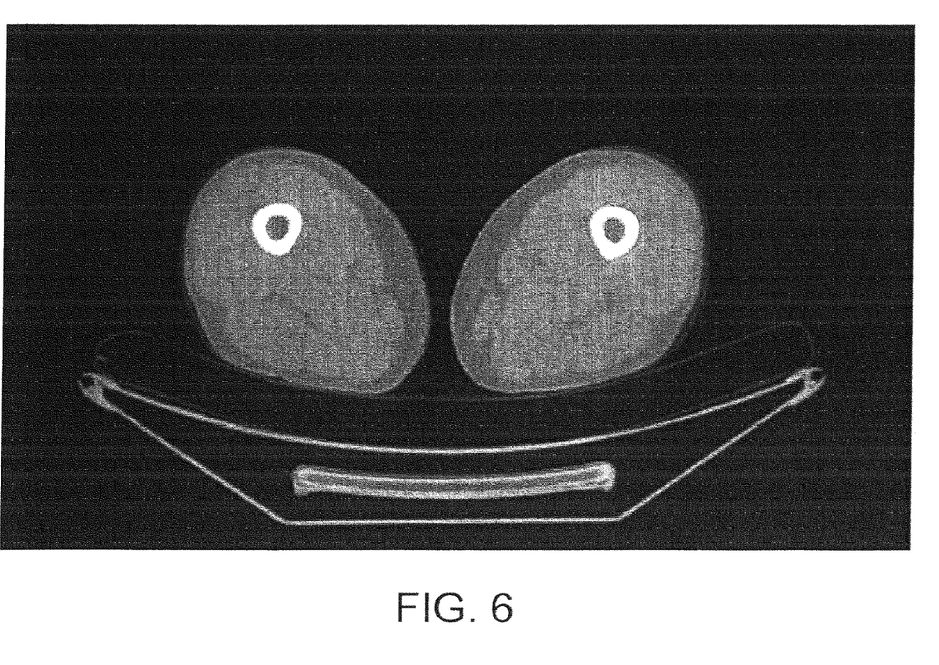
FIG. 6 is a CT image through thighs of the exemplary subject reconstructed from data acquired with saturated detectors that has been corrected using data from calibration detectors in accordance with the present invention.

Referring now to FIG. 5, a CT image through the thighs of an exemplary subject reconstructed from data of saturated detectors is shown. One skilled the art will readily appreciate the artifacts present in the image. These artifacts become more conspicuous when compared to the image of FIG. 6. The CT image of FIG. 6 is through the thighs of the exemplary subject wherein the data of saturated detectors has been corrected using the data of outer calibration rows. As is clear, correcting otherwise saturated data greatly improves image quality.

Figure 7:
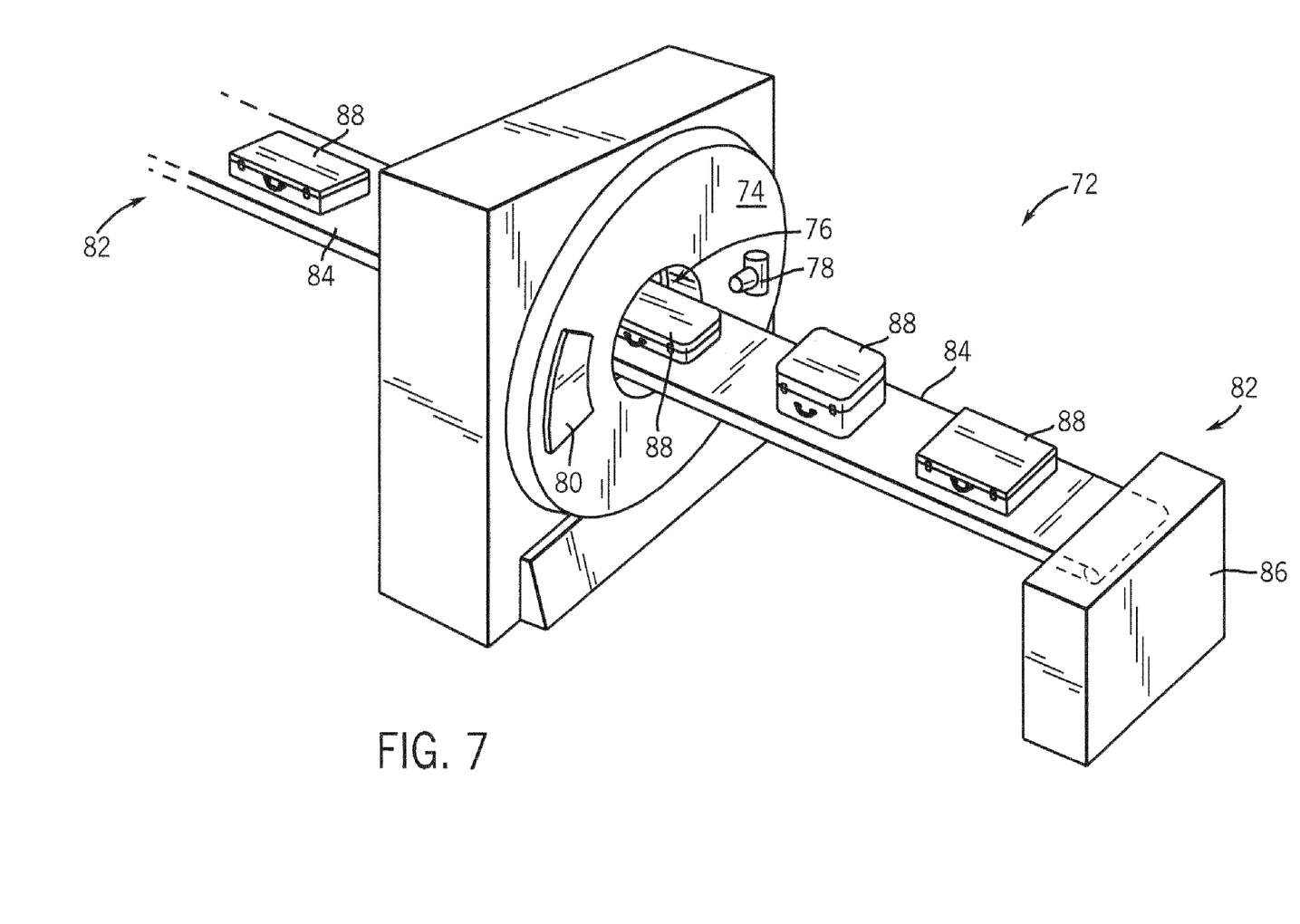
FIG. 7 is a pictorial view of a CT system for use with a non-invasive package inspection system.

Referring now to FIG. 7, package/baggage inspection system 72 includes a rotatable gantry 74 having an opening 76 therein through which packages or pieces of baggage may pass. The rotatable gantry 74 houses a high frequency electromagnetic energy source 78 as well as a detector assembly 80. A conveyor system 82 is also provided and includes a conveyor belt 84 supported by structure 86 to automatically and continuously pass packages or baggage pieces 88 through opening 76 to be scanned. Objects 88 are fed through opening 76 by conveyor belt 84, imaging data is then acquired, and the conveyor belt 84 removes the packages 88 from opening 76 in a controlled and continuous manner. As a result, postal inspectors, baggage handlers, and other security personnel may non-invasively inspect the contents of packages 88 for explosives, knives, guns, contraband, etc.

The present invention is directed to an over-range compensation system and technique that limits exposure to the full intensity of a radiation beam to less than all the rows of a multi-row radiation detector. In this regard, the present invention is particularly applicable for CT detectors that have difficulty in providing 1,000,000:1 dynamic range, i.e. CZT direct conversion detectors operating in current and/or single photon-counting modes. The present invention is also capable of controlling x-ray flux to satisfy the stringent dynamic range requirements of known charge integrating CT detector technologies. In addition to reducing detector costs, less data is required to be collected thereby improving data communication and data storage. Additionally, in contrast to implementation of water bags and rigid bowtie attenuators, the present invention maintains full image quality and, as shown with respect to FIGS. 5-6, can, in fact, improve image quality. Additionally, the present invention is applicable for the full range of body shapes and positioning within the scanner that can be encountered in a global population.

Therefore, a CT system is disclosed to include the radiation source configured to project radiation beamed toward a subject to be scanned. The CT system includes a collimator configured to collimate the radiation beam. There is a multi-row detector configured to detect radiation emitted by the radiation source and attenuated by the subject. A controller is operationally connected to the collimator and configured to control the collimator so as to limit exposure with full intensity of the radiation beam to less than all the detector rows of the multi-row CT detector.

The present invention also includes a radiographic imaging system having a multi-slice CT detector configured to detect radiation emitted by a radiation source and attenuated by a subject to be imaged. A slice-width collimator is disposed between the radiation source and the multi-slice CT detector. The collimator is used to collimate a radiation beaming a direction parallel to a long axis of the subject such that full intensity of the radiation beam is prevented from impending upon at least one intensity calibration detector row of the multi-slice CT detector.

A CT detector assembly is disclosed and includes a plurality of imaging CT detectors arranged into multiple CT detector rows. Data collected by the plurality of imaging CT detectors is used for image reconstruction. The CT detector assembly further includes a plurality of saturation correction CT detectors arranged into one or more saturation correction detector rows. Each saturation correction CT detector is constructed to over-range at an x-ray flux greater than that at which an imaging CT detector saturates.

The present invention also includes a radiographic imaging system having a single-slice CT detector configured to detect radiation emitted by a radiation source and attenuated by a subject to be imaged. A dynamic slice-width collimator is disposed between the radiation source and the single-slice CT detector. The dynamic collimator is used to collimate a radiation beam such that the radiation beam may be changed from full intensity to low intensity, for example on a view-by-view basis, in order to provide intensity calibration data from the single detector row of the single-slice CT detector.

The present invention has been described in terms of the preferred embodiment, and it is recognized that equivalents, alternatives, and modifications, aside from those expressly stated, are possible and within the scope of the appending claims.

What is claimed is:

1. A radiographic imaging system comprising:
    a single-slice CT detector having a single detector row and configured to detect radiation emitted by a radiation source and attenuated by a subject to be imaged;
    a dynamic slice-width collimator disposed between the radiation source and the single-slice CT detector and configured to collimate a radiation beam at a first position and a second position, wherein a total flux passed through the dynamic slice-width collimator at the first position is lower than a total flux passed through the dynamic slice-width collimator at the second position;
    a data acquisition system (DAS) configured to acquire non-saturated data from the single-slice CT detector with the dynamic slice-width collimator disposed at the first position, and configured to acquire imaging data with the dynamic slice-width collimator disposed at the second position; and
    a computer programmed to correct data received with the dynamic slice-width collimator at the second position using data received with the dynamic slice-width collimator at the first position.

2. The radiographic imaging system of claim 1 wherein the dynamic slice-width collimator is configured to provide intensity calibration detector data on a view-by-view basis.

3. A CT detector assembly comprising:
    a plurality of imaging CT detectors arranged into multiple CT detector rows, wherein data collected by the plurality of CT detectors is used for image reconstruction, the plurality of imaging CT detectors including at least one saturation correction CT detector row and a plurality of over-ranged CT detector rows;
    wherein the at least one saturation correction CT detector row is constructed to receive a non-saturating flux of x-rays; and
    a computer programmed to correct data from the plurality of over-ranged CT detector rows using data received from the at least one saturation correction CT detector row.

4. The CT detector assembly of claim 3 wherein the at least one saturation correction CT detector row is impinged by only a penumbral region of a radiation beam.

5. The CT detector assembly of claim 3 wherein the at least one saturation correction CT detector row includes a first row of saturation correction CT detectors at a fore end of the multiple CT detector rows and a second row of saturation correction detectors at an aft end of the multiple CT detector rows.

6. The CT detector assembly of claim 3 wherein the at least one saturation correction CT detector row includes a single saturation correction CT detector row.

7. The CT detector assembly of claim 6 wherein the single row of saturation correction detectors is centrally positioned between a pair of center-most rows of the plurality of over-ranged CT detector rows.

8. The CT detector assembly of claim 3 further comprising a slice-width collimator disposed between a radiation source and the plurality of imaging CT detectors.

9. The CT detector assembly of claim 3 wherein the plurality of imaging CT detectors further comprise a direct conversion material.

10. A radiographic imaging system comprising:
    a radiation source configured to project a radiation beam toward a subject to be scanned; and
    a detector configured to detect radiation emitted by the radiation source and attenuated by the subject, the detector comprising:
        a plurality of rows of saturated detector elements receiving a saturating flux; and
        at least one row of non-saturated detector elements receiving a non-saturating flux; and
    a computer programmed to correct data received from the plurality of rows of saturated detector elements based on data received from the at least one row of non-saturated detector elements.

11. The radiographic imaging system of claim 10 wherein the detector further comprises two rows of non-saturated detector elements, wherein one row of non-saturated detector elements is located at a forward end and another row of non-saturated detector elements is located at a rear end of the detector.

12. The radiographic imaging system of claim 10 further comprising a collimating element positioned between the radiation source and the detector to attenuate x-rays impinging upon a single detector row of the detector so that the single detector row is not exposed to a full intensity of a radiation beam emitted from the radiation source.

13. The radiographic imaging system of claim 12 wherein the collimating element is centrally positioned between a pair of rows of non-saturated detector elements of the detector.

14. The radiographic imaging system of claim 10 wherein the detector further comprises a direct conversion material.

15. The radiographic imaging system of claim 10 wherein the radiographic imaging system is a CT imaging system.

16. A CT system comprising:
a CT detector assembly comprising:
- a plurality of imaging CT detectors arranged into multiple CT detector rows;
- a plurality of saturation correction CT detectors arranged into one or more saturation correction detector rows; and a data acquisition system (DAS) configured to:
- receive imaging data from the plurality of imaging CT detectors;
- receive saturation correction data from the plurality of saturation correction CT detectors; and
- correct saturated data in the imaging data using the saturation correction data.

17. The CT system of claim 16 wherein the one or more saturation correction detector rows include two correction detector rows, one correction detector row at a fore end and another correction detector row at an aft end of the plurality of CT detector rows.

18. The CT system of claim 16 wherein the one or more saturation correction detector rows include a single correction detector row.

19. The CT system of claim 18 wherein the single correction detector row is centrally positioned between a pair of center-most CT detector rows of the plurality of CT detector rows.

20. The CT system of claim 16 wherein a saturation correction detector is sized to be smaller than an imaging CT detector.

* * * * *